United States Patent

Staples et al.

[11] Patent Number: 6,050,148
[45] Date of Patent: Apr. 18, 2000

[54] DYNAMIC STRENGTH TESTER FOR PAPER CORES

[75] Inventors: John Freeman Staples, Blythewood, S.C.; Dennis Taylor, King, N.C.; Johannes W. van de Camp, HW Meerssen, Netherlands; Steve Lyles; Jason T. Stephens, both of Hartsville, S.C.

[73] Assignee: Sonoco Development, Inc., Hartsville, S.C.

[21] Appl. No.: 09/106,243

[22] Filed: Jun. 29, 1998

[51] Int. Cl.[7] .................................................. G01N 3/08
[52] U.S. Cl. ................................................. 73/829; 73/857
[58] Field of Search .............................. 73/824, 829, 833, 73/837, 843, 845, 856, 857, 858, 859

[56] References Cited

U.S. PATENT DOCUMENTS

| | | |
|---|---|---|
| 2,650,493 | 9/1953 | Bowen, Jr. et al. . |
| 3,662,591 | 5/1972 | Bons . |
| 3,680,366 | 8/1972 | Moser et al. . |
| 3,736,795 | 6/1973 | Andersson .......................... 73/862.632 |
| 3,797,304 | 3/1974 | Klinger et al. . |
| 3,908,448 | 9/1975 | Jardine et al. . |
| 4,738,145 | 4/1988 | Vincent et al. ....................... 73/862.23 |
| 4,819,488 | 4/1989 | Morel . |
| 5,339,693 | 8/1994 | Rowlands et al. .......................... 73/825 |
| 5,379,648 | 1/1995 | Tiffin . |

FOREIGN PATENT DOCUMENTS

| | | |
|---|---|---|
| 0 309 123 | 8/1988 | European Pat. Off. . |
| P 15232 IX/42k | 7/1956 | Germany . |
| 363016 | 5/1973 | Russian Federation . |

OTHER PUBLICATIONS

Filatov et al, "Machine for the Programmed Fatigue Testing of Specimens Under Axial Loading", Dec. 1969, 3 pages.

*Primary Examiner*—Max Noori
*Attorney, Agent, or Firm*—Alston & Bird LLP

[57] ABSTRACT

A testing apparatus for determining dynamic strength of sample paper cores includes a rotatably driven pneumatic chuck for engaging the inner surface of a sample core to rotatably drive the sample core, and a variable-tension belt assembly having a flexible belt which is looped over the sample core and tensioned to simulate the load applied to a paper core in actual use. The belt is tensioned by a pneumatic cylinder which is controlled under feedback control by a servo valve and a computer controller so that the load applied to the sample core accurately tracks a predetermined desired load schedule versus time.

22 Claims, 7 Drawing Sheets

DYNAMIC STRENGTH TESTER FOR PAPER CORES

FIELD OF THE INVENTION

The present invention relates to an apparatus and method for determining the dynamic strength of a tubular member and, more particularly, to an apparatus and method for determining the dynamic strength of a sample of a paper core of the type used for winding large rolls of web material such as paper, film, or the like.

BACKGROUND OF THE INVENTION

Paper manufacturers typically supply paper to converters in the form of large rolls wound on cores, and the converters finish the paper into newsprint, magazine stock, and other products which are then sold to printers for printing newspapers, magazines, and the like. The gravure and offset printing presses in common use today are continually being improved to increase their speed as well as their width, in a constant effort to increase throughput and reduce the frequency of roll changes. To meet the demands of these faster and wider presses, paper manufacturers are producing larger and wider rolls of paper.

In general, the industry prefers paper to be wound on paper cores as opposed to cores made of other materials such as steel. Accordingly, paper cores are being subjected to greater and greater loads as paper rolls are increased in size to meet the demands of faster and wider presses. These greater loads can lead to failure of the paper core if it is not properly designed and manufactured.

A paper roll is typically supported on a winder or within a press by a pair of slip-fit or expandable mandrels which are inserted into each end of the paper core and engage the inner surfaces of the core. The mandrels are rotatable to permit the paper roll to rotate as required during a winding or unwinding operation. As the paper roll is rotated, a dynamic or cyclic load is imposed on any given region of the paper core, alternating between compression when the region is on top of the core and tension when the core is rotated to bring the region toward the bottom of the core. The heavy cyclic loading of the core can lead to delamination failure of the core, either by ply bond separation or by adhesive failure. The general term for such failures is dynamic strength failure.

Efforts have been made to develop testing devices for determining the dynamic strength of paper cores. For example, U.S. Pat. No. 4,819,488 issued to Morel discloses an apparatus for testing the resistance to cleavage of cardboard tubes. The device includes a rotatably mounted mandrel which has four narrow keying jaws equally spaced about its outer circumference, the jaws being outwardly expandable by turning an adjustment screw. A sample tube is fitted within a metal sleeve having an inside diameter just slightly larger than the outside diameter of the tube, the metal sleeve being intended to simulate the roll of paper wound around the tube. The assembly of the sleeve and sample tube are placed over the mandrel and the adjustment screw is operated to cause expansion of the jaws to engage the inner surface of the tube so as to compress the wall of the tube between the jaws and the metal sleeve. A drive belt is looped about the outer surface of the metal sleeve. The drive belt is stretched between the sleeve and a drive pulley mounted on a drive shaft which is spaced from and parallel to the rotation axis of the mandrel and is rotatably supported by a pivotal frame. The drive pulley is rotatably driven by a motor. Thus, the metal sleeve is rotatably driven by the drive belt and motor, and the sample tube is in turn rotatably driven by the frictional engagement of the metal sleeve with the outer surface of the tube. A pneumatic jack is connected to the pivotal frame and is operable to cause pivotal motion of the frame so as to change the distance between the rotation axis of the mandrel and the axis of rotation of the drive shaft, thereby changing the tension in the drive belt. Thus, the load is imposed on the tube by the inner surface of the metal sleeve, which transmits the load imposed on it by the drive belt. The variable tensioning of the belt is intended to simulate varying weight of a paper roll wound on the tube.

The testing apparatus disclosed in the Morel patent does not accurately simulate the type of loading experienced by a paper core in actual use. More specifically, it can be shown that variation in fit between the outer surface of the test sample and the inner surface of the metal sleeve affects the test results. Since manufacturing tolerances for paper cores can lead to significant variations in outer diameters, this sensitivity to outer diameter represents a significant problem. Furthermore, paper cores are made in a substantial number of different nominal outer diameters, and therefore the Morel apparatus requires that many sleeves of different inside diameters be kept on hand in order to match the test sample with a sleeve of the proper inside diameter.

Additionally, the metal sleeves are quite rigid, and it can be shown that this rigidity adds support to the test sample, thus altering the test results and making detection of defects more difficult. The Morel device also does not include any provision for accurately measuring and controlling the load imposed on the test sample by the variable-tension belt. Moreover, driving the sample by frictional engagement with the inner surface of the sleeve is not representative of the manner in which a paper core is driven in actual use. Yet another problem with the Morel device is that the mandrel differs greatly from the mandrels used in the industry. The keying jaws of the Morel mandrel are quite narrow, the four jaws combined contacting only about 35 percent of the circumference of the test sample. Thus, expansion of the jaws can destroy the paper in the areas where the jaws contact the inner surface of the sample. Further, the load on the test sample causes concentrated compressive forces on the wall of the sample where the jaws contact the inner surface. Both of these mechanisms can significantly alter the test results, or even cause failure of the sample before the test even begins.

SUMMARY OF THE INVENTION

The present invention overcomes the aforementioned drawbacks associated with prior paper core testing devices by providing a testing apparatus and method in which a sample paper core is supported by a driving element which engages the inner surface of the sample paper core and is rotatably driven by a motor to cause rotation of the sample. The apparatus includes a variable-tension belt assembly having an endless flexible belt which is wrapped partially around the outer surface of the sample paper core, directly contacting the sample. The variable-tension belt assembly further includes an actuator which is adapted to apply tension to the belt so as to impose a load on the sample paper core normal to the axis of the paper core, thus simulating the weight of a roll of paper or other material wound on the paper core. The apparatus is controlled by a controller which supplies a control signal to the actuator for controlling the tension applied to the belt as a function of time. Thus, changing loads experienced by a paper core during actual use may be accurately simulated. The flexible belt in contact with the sample paper core simulates the pliable paper wound around a core better than the metal sleeve used with prior testing apparatus. Furthermore, the sample is rotatably driven from the inside by the driving element, just as a core in actual use in a press is driven from the inside, thus better simulating the types of loads experienced by a core in actual use.

The apparatus preferably includes a load cell for measuring the actual force imparted on the belt by the actuator. The load cell supplies an output signal to the controller, and the controller operates in a feedback loop to drive the actual force toward a desired level of force.

The actuator preferably is a pneumatic cylinder. A servo valve supplies pressurized gas to the pneumatic cylinder and is connected to the controller, which controls the operation of the servo valve via the feedback loop so as to maintain the actual force on the belt substantially at the desired level of force.

The motor is a variable-speed motor and is connected to the controller, and a proximity sensor associated with the rotating driving element provides an output signal to the controller indicating revolutions of the driving element. The controller preferably is a microprocessor-based controller, such as a computer or computer/PLC (programmable logic controller) combination. The controller may be programmed to operate the pneumatic cylinder and the motor according to predetermined schedules of load and speed versus time so as to accurately simulate time-varying load and speed experienced by a paper core during actual use.

The driving element which engages the sample paper core preferably is a pneumatic chuck which has outwardly expandable leaves. The leaves are expandable over a range of outward movement so as to be engageable with sample paper cores of various inside diameters. Furthermore, the force imparted on the inner surface of the sample paper core by the leaves is selectively variable by varying the air pressure supplied to the pneumatic chuck.

BRIEF DESCRIPTION OF THE DRAWINGS

Additional objects, features, and advantages of the invention will become apparent from the following detailed description of a specific embodiment thereof, taken in conjunction with the accompanying drawings in which.

DETAILED DESCRIPTION OF THE DRAWINGS

FIGS. 1–4 depict various views of a testing apparatus 10 in accordance with the principles of the invention. The apparatus 10 includes a frame or chassis 12 which provides structural support to the various components of the apparatus. A motor 14 (FIG. 4) is mounted on a horizontal plate 16 of chassis 12, with an output shaft 18 of the motor 14 extending horizontally toward the back side of the apparatus 10. The output shaft 18 has a drive pulley 20 mounted thereon.

A drive shaft 22 (FIG. 3) is rotatably supported in a horizontal orientation parallel to and spaced vertically above the motor output shaft 18. The drive shaft 22 is supported by tapered roller bearings 24 contained within a pair of horizontally spaced bearing blocks or housings 26 which are secured to a horizontal plate 28 of the chassis 12. A timing pulley 30 is mounted on the drive shaft 22 adjacent the end nearest the back side of the apparatus 10, the timing pulley 30 being horizontally aligned with the drive pulley 20. A timing belt 32 is looped around the drive pulley 20 and the timing pulley 30. Thus, the drive shaft 22 is rotatably driven by the timing pulley 30 and timing belt 32 via connection of the belt 32 with drive pulley 20. The timing pulley 30 advantageously is larger in diameter than the drive pulley 20 so as to effect a speed reduction between the motor output shaft 18 and the drive shaft 22, for example about a 3:1 speed reduction.

Figure 1:
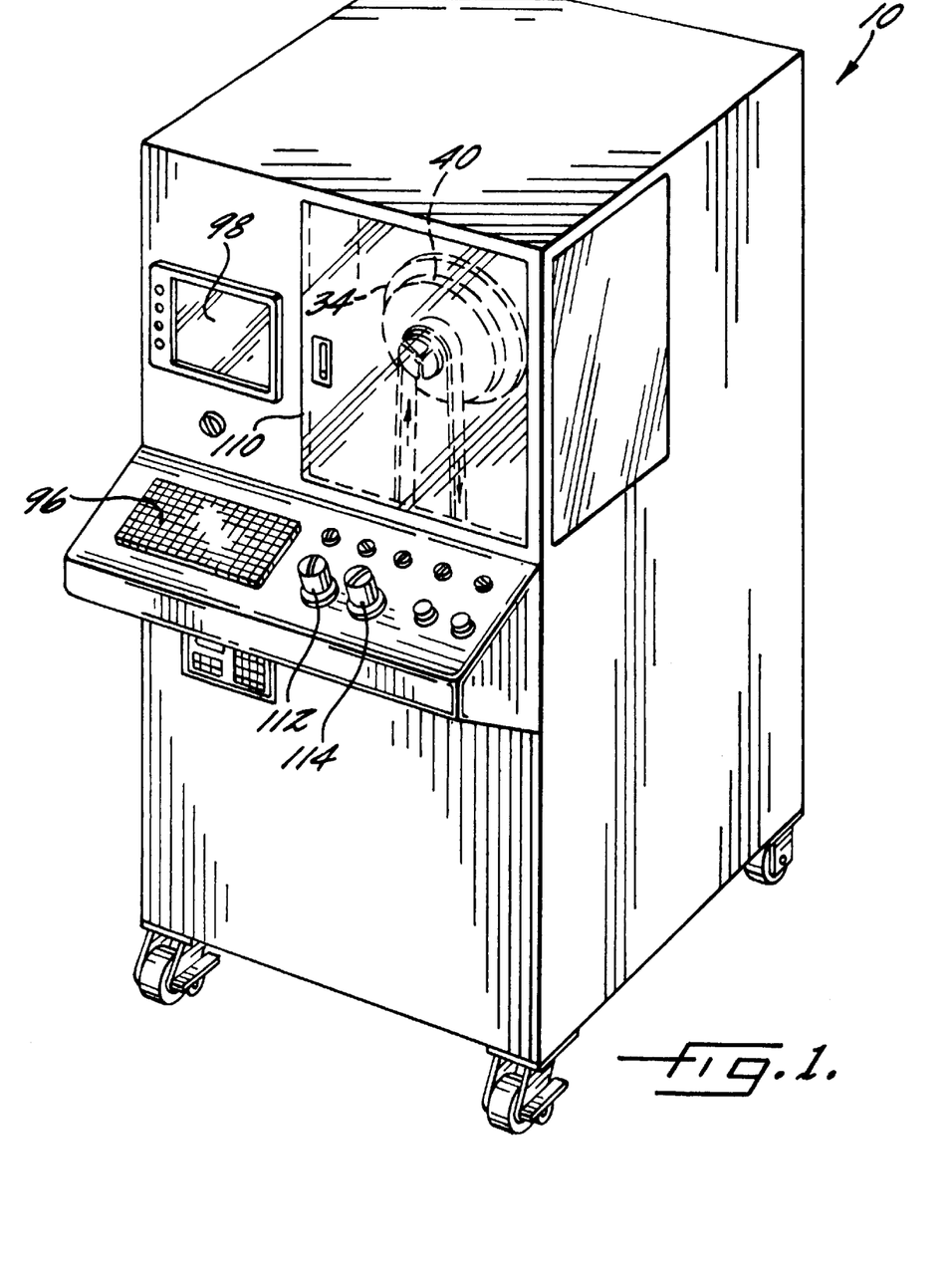
FIG. 1 is a perspective view of a testing apparatus in accordance with the principles of the invention.
Figure 2:
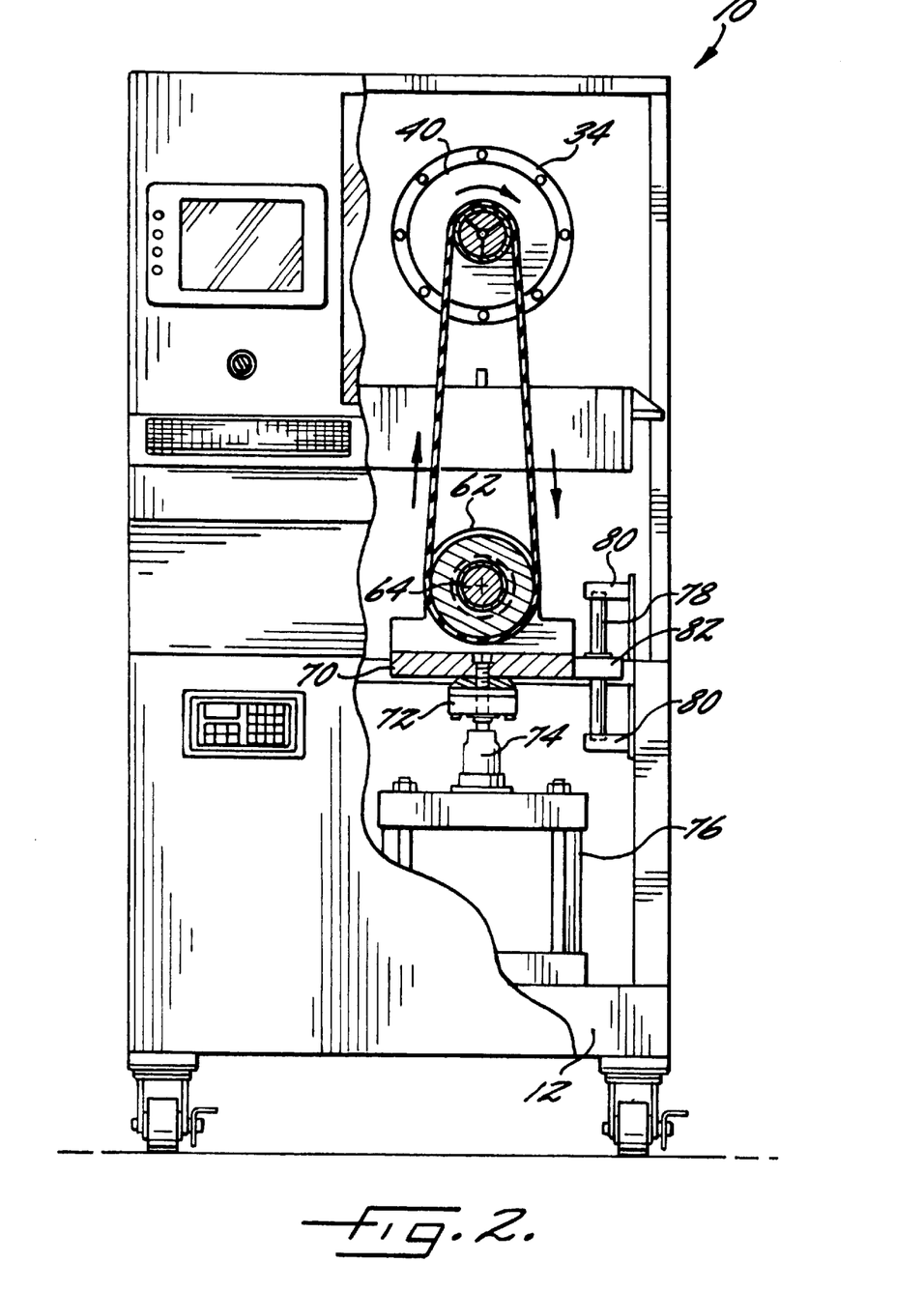
FIG. 2 is a front elevation of the testing apparatus partially broken away to show internal details of the apparatus.
Figure 3:
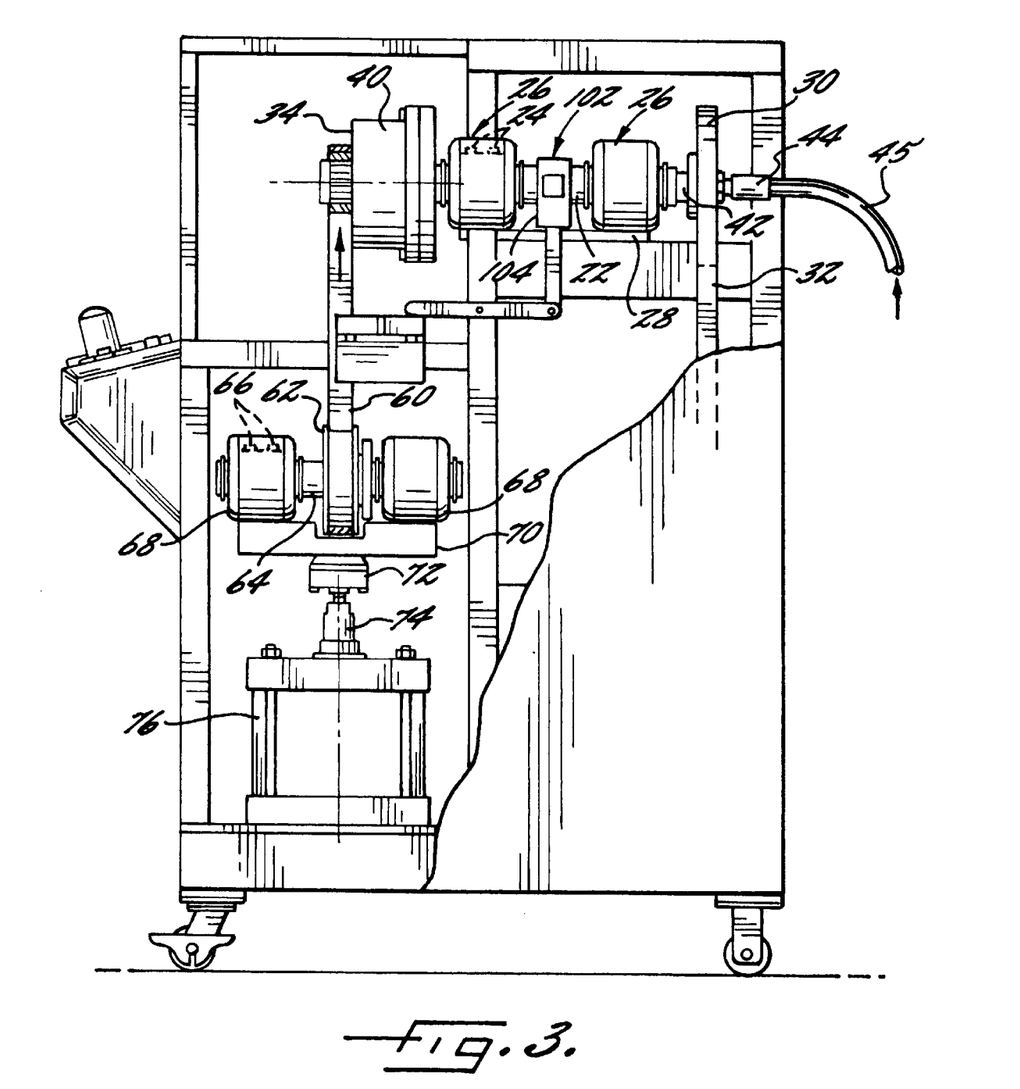
FIG. 3 is a left-side elevation of the testing apparatus partially broken away to shown internal details of the apparatus.
Figure 4:
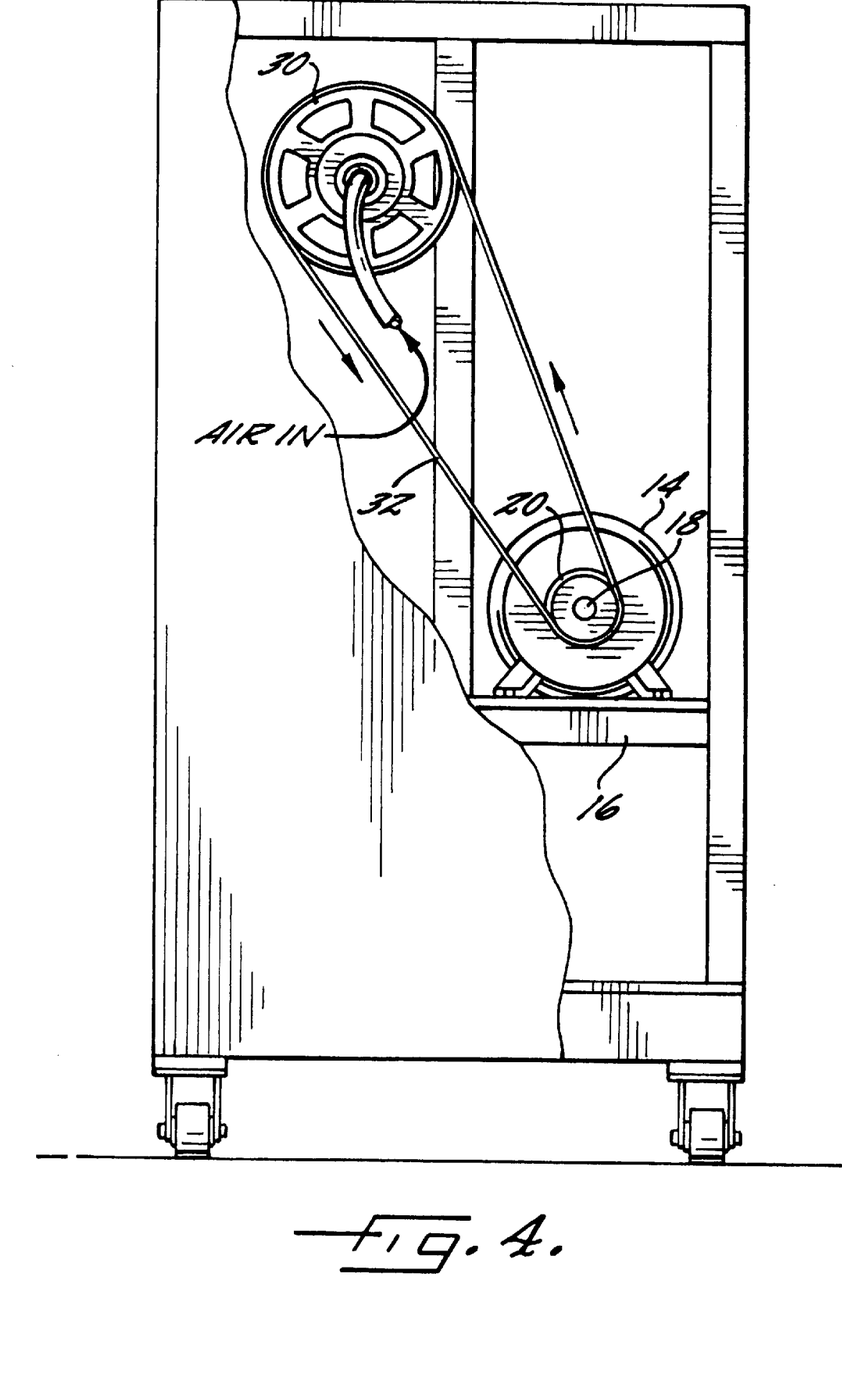
FIG. 4 is a rear elevation of the testing apparatus partially broken away to show the drive motor's connection to the drive shaft.

The opposite end of the drive shaft 22 nearest the front side of the apparatus 10 supports a pneumatic chuck 34 (FIGS. 1 and 2). The pneumatic chuck 34 is keyed or otherwise secured to the drive shaft 22 so that it rotates with the drive shaft 22.

The drive shaft 22 includes an internal passage 42 extending centrally therethrough along the entire length of the shaft 22 for supplying pressurized air to the pneumatic chuck 34. A pneumatic rotary union 44 is connected to the rear end of the shaft 22 and is adapted to be connected to a suitable air supply line 45 and to supply air from the line 45 into the internal passage 42.

The pneumatic chuck 34 includes a set of three leaves 46 (FIGS. 5–9) which are outwardly expandable over a range of radial movement for accommodating variations in inside diameter of sample cores. The leaves 46 are configured to be generally circular-arc shaped at their outer surfaces, each leaf spanning an arc of about 110 degrees, so that collectively the leaves 46 contact over 90 percent of the circumference of a sample paper core inner surface. The leaves 46 are interconnected by springs (not shown) which assist in evenly distributing the forces imposed by the leaves 46 on a sample core.

Figures 5, 6:
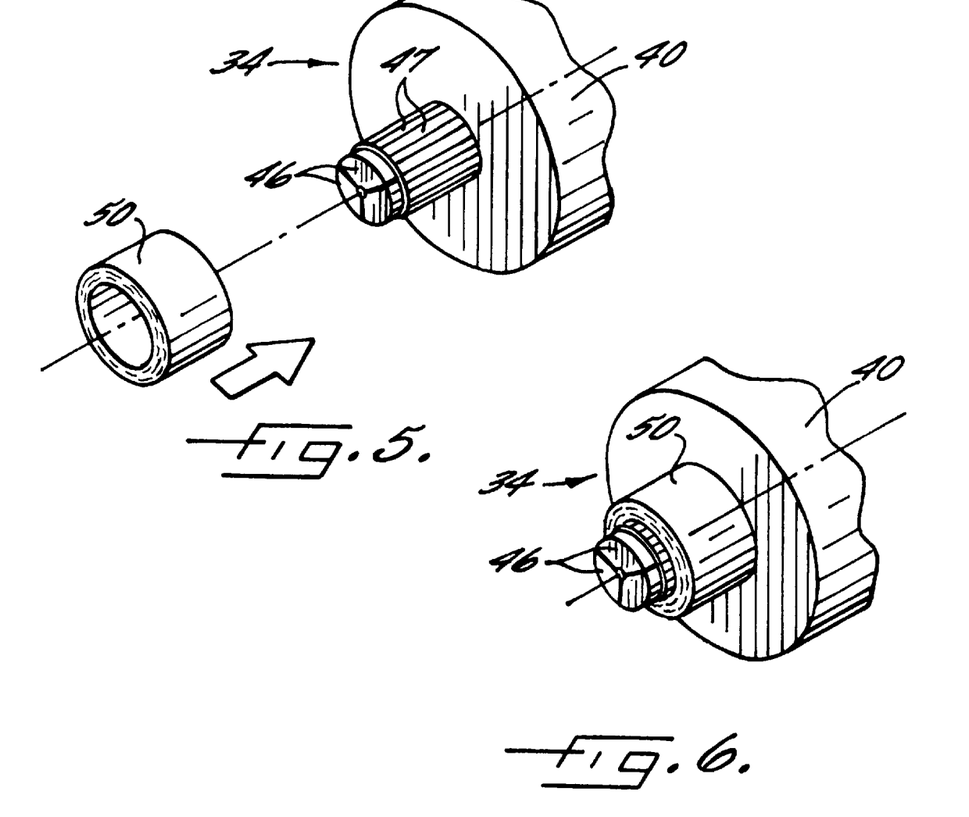
FIG. 5 is a perspective view showing a sample paper core being placed on the unexpanded pneumatic chuck.
FIG. 6 is a view similar to FIG. 5 showing the sample paper core in place on the unexpanded chuck.

FIG. 5 depicts the pneumatic chuck 34 showing a sample paper core 50 being mounted on the chuck 34. The chuck 34 is removable from the drive shaft 22 (FIG. 3) and replaceable with similarly designed chucks configured for different sizes of core. Thus, a variety of sizes of cores can be tested. Advantageously, the leaves 46 of the chuck 34 include longitudinal ribs 47 which facilitate gripping of the sample core 50 from the inside so that the core 50 does not rotatably slip with respect to the chuck 34.

Figure 7:
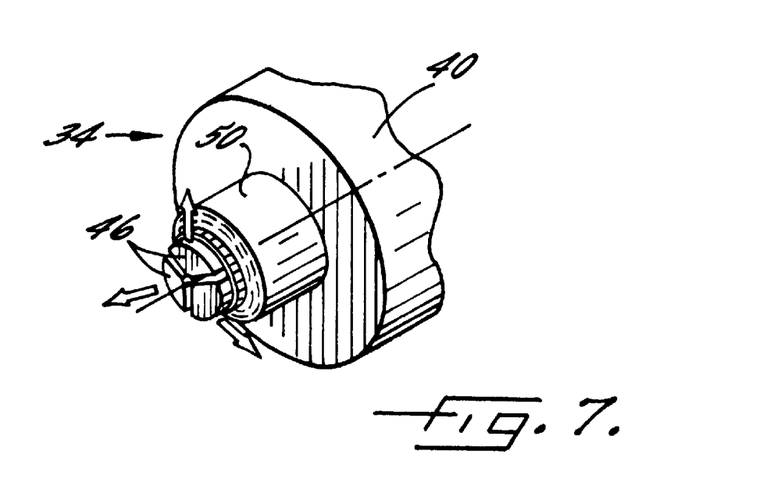
FIG. 7 is a view similar to FIG. 6, showing the chuck expanded to engage the inner surface of the sample paper core.

FIG. 6 shows the sample core 50 in place on the chuck 34 with the leaves 46 in the unexpanded position, and FIG. 7 shows the leaves 46 expanded outwardly to engage the inner surface of the sample core 50.

Load is imposed on the sample paper core 50 by an endless flexible belt 60 which is wrapped partially around the outer surface of the sample core 50 and around a pulley or sheave 62 (FIGS. 2, 3, and 9) which is selectively movable so as to vary the tension applied to the belt 60. More specifically, the sheave 62 is mounted on a lower shaft 64 which is rotatably supported by bearings 66 contained in housings 68 which are mounted on a vertically slidable support plate or transducer plate 70. The transducer plate 70 is vertically supported by and affixed to a load cell 72 which is connected to the piston 74 of a pneumatic cylinder 76. Thus, upon extension of the piston 74, the load cell 72 and transducer plate 70 are translated upwardly, decreasing the distance between the axes of the pneumatic chuck 34 and the lower shaft 64 and accordingly reducing the tension in the belt 60. Conversely, upon retraction of the piston 74, the load cell 72 and transducer plate 70 are translated downwardly so that tension in the belt 60 is increased. Vertical movement of the transducer plate 70 is guided by a guide cylinder 78 (FIG. 2) vertically mounted by a pair of brackets 80 affixed to the chassis 12. A guide yoke or collar 82 engages the guide cylinder 78 and is attached to the transducer plate 70. The guide collar 82 slides vertically along the guide cylinder 78 so that movement of the transducer plate 70 is constrained to be in the vertical direction.

The apparatus 10 includes a control system that enables the load imposed on a sample paper core by the belt 60 to be accurately controlled to match any desired level of force, and which also enables the force to be varied as a function of time during a test. To these ends, and with reference to FIG. 10, the pneumatic cylinder 76 is supplied with pressurized gas, preferably air, from a suitable source via a controllable servo valve 84. Further, the load cell 72 provides an output signal, via a conventional bridge circuit, as a function of the force exerted between the transducer plate 70 and the pneumatic cylinder 76. The load cell 72 is zeroed out at static condition with the belt 60 slack, so that the force indicated by load cell 72 is equal to the force exerted on a sample paper core by the belt 60.

Figure 10:
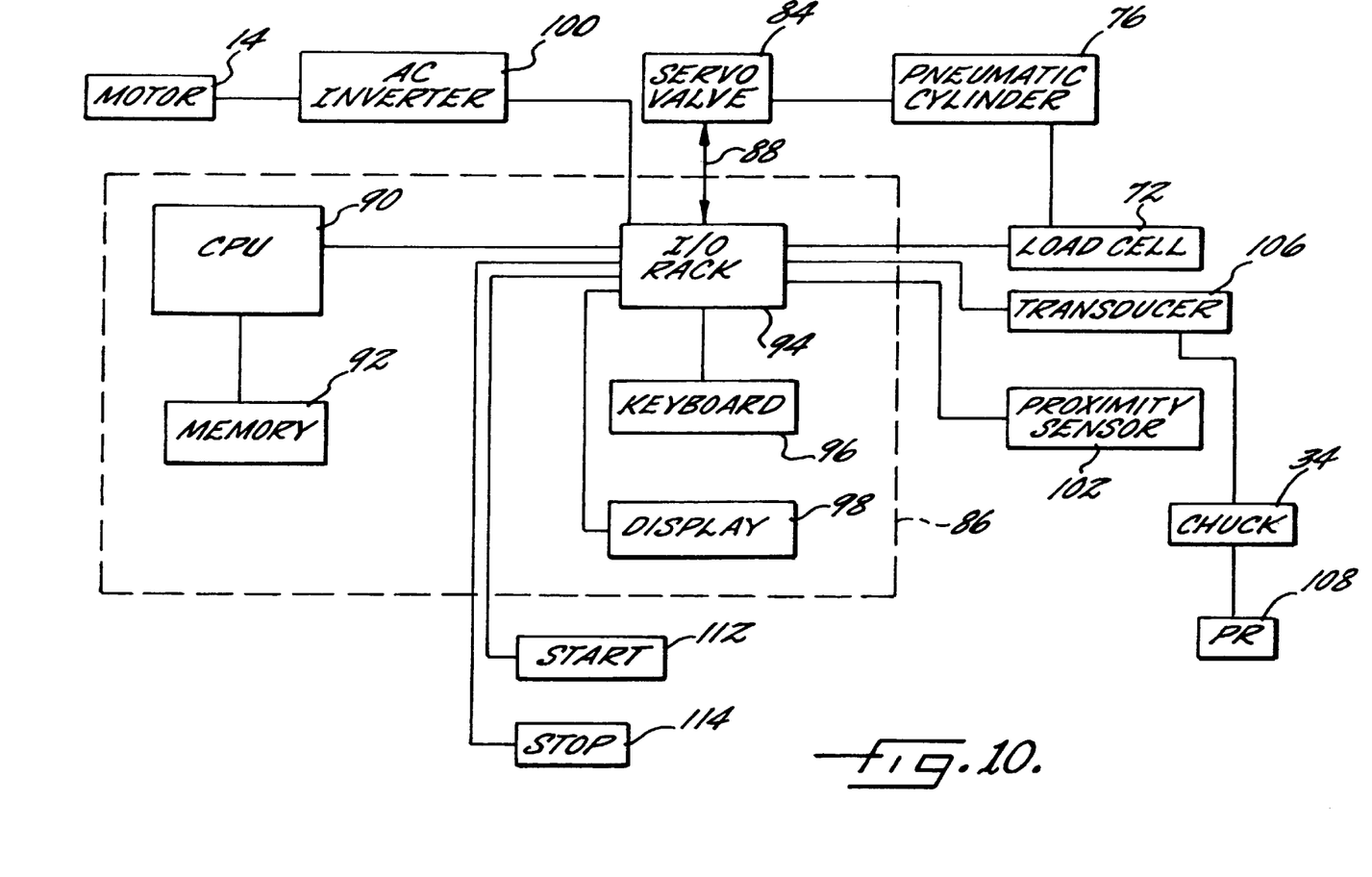
FIG. 10 is a schematic representation of the control system showing the connections between the controller and the sensors and controlled devices of the apparatus.

The output signal from the load cell 72 is supplied to a microprocessor-based controller 86, which is also connected via a control line 88 to the servo valve 84.

The controller 86 is a combination of a programmable logic controller (PLC) and a PC, although other types of microprocessor-based controllers could be used. In conventional fashion, the controller 86 includes a CPU 90, memory unit 92, remote I/O rack 94, a keyboard 96, and a display 98. The controller 86 is programmed with control logic for operating the servo valve 84 in a feedback loop so as to control the force exerted by pneumatic cylinder 76 to track a predetermined desired force function which is entered into memory unit 92 via the operator keyboard 96.

The servo valve 84 advantageously is set up to provide zero pressure at zero volts of input and 5 bar of pressure at 10 volts of input. The servo valve 84 does not require calibration, other than to assure that it provide zero pressure at zero volts, since the actual load measured by load cell 72 is constantly compared to the desired load and, if different, the input voltage to servo valve 84 is adjusted to drive the actual load toward the desired load.

The apparatus 10 permits variable-speed operation of the motor 14. An AC inverter 100 controls the motor 14, allowing motor speed to be varied to effect chuck speeds of from about 400 to about 1000 rpm. A proximity sensor 102 (FIGS. 3 and 10) mounted via a bracket 104 adjacent the drive shaft 22 provides a per-revolution output signal to the controller 86, which the controller 86 converts into revolutions per minute of shaft 22 and displays on the display 98.

The apparatus 10 also includes a pressure transducer 106 which provides an output signal as a function of the pressure applied to the pneumatic chuck 34. The pressure applied to the chuck 34 is manually adjustable via a pressure regulator 108. However, the pressure is measured by transducer 106 and fed to the controller 86 for display on display unit 98.

Figures 8, 9:
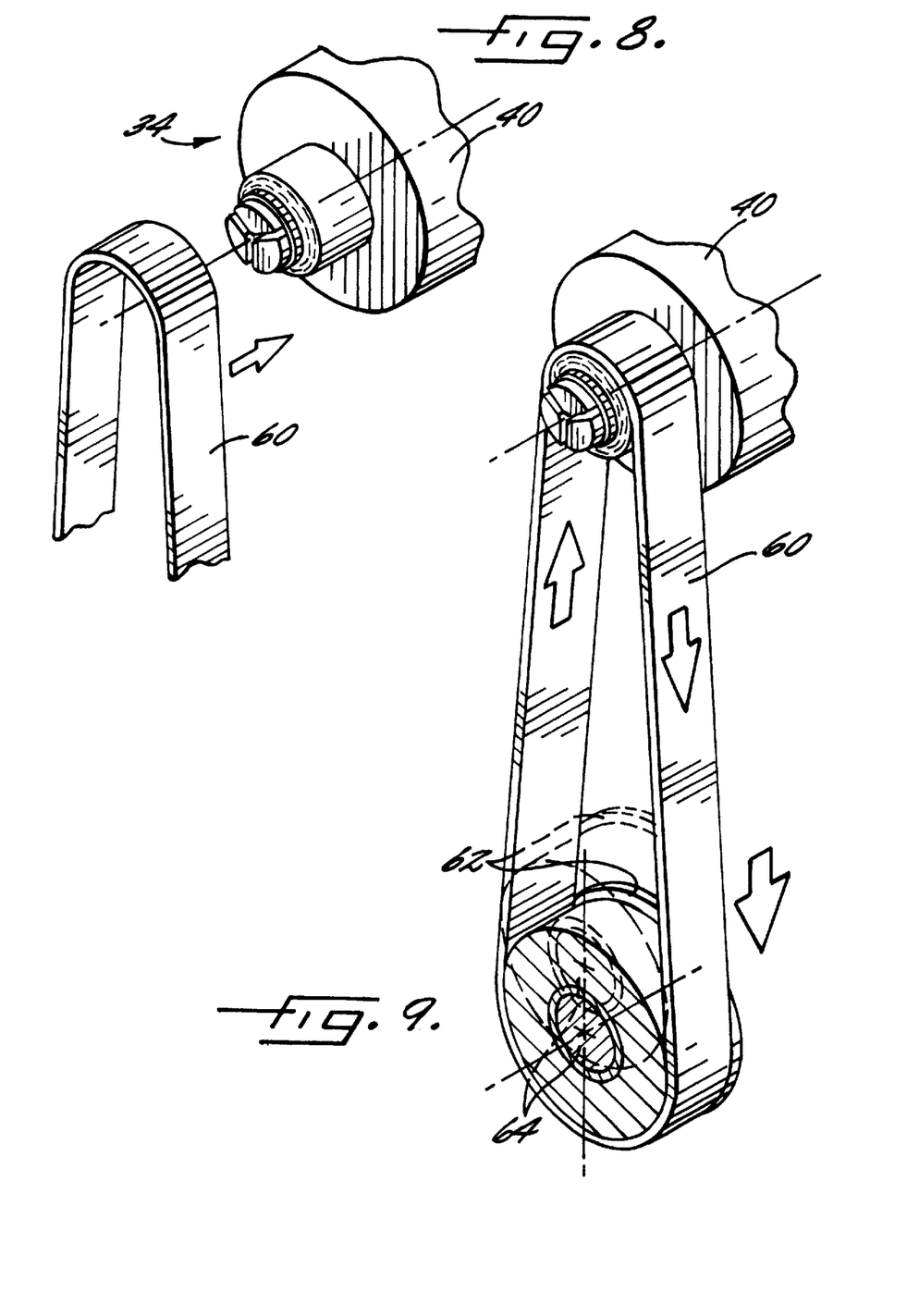
FIG. 8 is a view similar to FIG. 7, showing the belt being placed around the sample paper core.
FIG. 9 is a view similar to FIG. 8, showing the belt in tension for applying a load to the sample paper core.

The apparatus 10 may be operated either in manual mode or automatic mode. To begin a test, the operator opens a door 110 (FIG. 1) to gain access to the pneumatic chuck 34 and belt 60. A safety switch (not shown) prevents operation of the motor 14 and pneumatic cylinder 76 when the door is open. Thus, upon opening of the door 110, the belt 60 is slack, as indicated by the position of sheave 62 shown in phantom lines in FIG. 9. The operator places a sample paper core 50 on pneumatic chuck 34 (FIGS. 5 and 6) and closes the door 110, and operates the pressure regulator 108 to expand the the leaves of the chuck to engage the inner surface of the sample core (FIG. 7). The pressure applied to the chuck 34 is displayed on display unit 98, allowing the operator to adjust pressure regulator 108 to achieve a predetermined desired pressure. The belt 60 is looped over the sample core 50 and around the sheave 62 (FIGS. 2 and 9).

The operator uses the keyboard 96 to select either manual or automatic mode of operation. For automatic mode, the operator enters a desired pre-load force to be applied to the core 50, the chuck pressure, the chuck rpm, and the load rate or schedule (e.g., load versus time or rate of load increase with time). For example, a pre-load of 15 kN may be entered, along with a load ramp rate of 0.3 kN per second, so that upon start of the test, the load will begin at 15 kN and ramp upwardly at 0.3 kN per second. Controller 86 also prompts the operator to enter identifying information about the test, such as a sample ID number. The operator then closes the door, whereupon the pneumatic cylinder 76 pre-loads the belt 60 according to the pre-load entered by the operator.

Next, the operator presses a start button 112 (FIGS. 1 and 10), and the controller 86 operates the motor 14 and pneumatic cylinder 76 according to the selected speed and load rate. The operator visually inspects the sample core 50 for failure and, when a failure is detected (which is usually both visually and audibly manifested), he presses a stop button 114. Upon receiving a stop signal from stop button 114, the controller 86 stops the motor 14 and closes the servo valve 84, and computes the elapsed time to failure (via internal system clock), the number of revolutions to failure, and the load at failure. The operator is prompted to enter certain information about the failure mode, such as radial distance from the inside diameter of core 50 to the point of failure, and a description of the failure mode. All of these computed and entered data and the setup data (i.e., chuck pressure, pre-load force, chuck rpm) and identifying information are stored in memory 92 and are displayed on display unit 98. The control software also allows the operator to export the data to a common file format that can be used with other spreadsheet or word processor software.

In manual mode of operation, non-standard tests can be performed. For instance, the core may be loaded with a pre-load or load rate with the core held stationary (i.e., not rotating), or the belt tension may be manually adjusted via a pressure regulator (not shown).

There have thus been described a paper core dynamic strength testing apparatus and method which provide unique advantages over prior testing apparatus and methods, including the abilities to accurately control and vary the load applied to a test sample during the course of a test, to more closely simulate the load distribution applied to a paper core by the pliable paper wound thereon via a flexible belt which directly contacts the outer surface of the sample core, to engage a sample core with a pneumatic chuck which evenly distributes the engaging forces over the circumference of the core's inner surface and which is adjustable to vary the chuck pressure and degree of chuck expansion, and to record, store, and display all pertinent data and information about a given test. Other advantages of the invention will also be apparent from the foregoing description.

While the invention has been explained by reference to a specific embodiment thereof, the invention is not limited to the particular apparatus and method illustrated and described herein. Other embodiments falling within the scope of the invention will be readily apparent to those of ordinary skill in the art. For example, any suitable actuator may be used to serve the purpose of the pneumatic cylinder 76, such as a servo or other motor, with or without gears, as long as the actuator is capable of being controlled to accurately impart a desired force on the belt. Likewise, any suitable driving device may be used to serve the purpose of the pneumatic chuck 34, as long as it is capable of engaging the core uniformly and evenly so as not to fail the core or skew the test results, and is capable of being adjusted to accommodate variations in core inside diameter. Additionally, although the description has referred to the testing of dynamic strength of a sample paper core, the apparatus and method of the invention can also be used for testing core adhesion and tube quality. Other modifications are also possible. Accordingly, the scope of the invention including such other embodiments and modifications is to be determined by the appended claims.

What is claimed is:

1. An apparatus for testing dynamic strength of a sample paper core, comprising:
    a motor;
    a driving element rotatably driven by the motor about a rotational axis, the driving element being adapted to coaxially engage an inner surface of the sample paper core such that rotation of the driving element causes rotation of the sample paper core about a longitudinal axis thereof;
    a variable-tension belt assembly including an endless flexible belt adapted to be wrapped partially around an outer surface of the sample paper core, and an actuator adapted to apply tension to the belt so as to impart a load on the sample paper core; and
    a controller adapted to control the actuator for controlling the tension of the belt.

2. The apparatus of claim 1, further comprising a load cell connected to the actuator, the load cell providing an output signal as a function of the amount of force imparted to the belt by the actuator, the controller receiving the output signal from the load cell and controlling the actuator via a feedback loop so as to drive the force imparted to the belt toward a desired level of force.

3. The apparatus of claim 2 wherein the actuator is a pneumatic cylinder, and further comprising a servo valve connected to the pneumatic cylinder and adapted to supply pressurized gas thereto from a suitable source, the controller controlling the belt tension by controlling the servo valve so as to control the gas pressure delivered through the servo valve to the pneumatic cylinder.

4. The apparatus of claim 3 wherein the motor is a variable-speed motor and the controller is adapted to control the rotational speed of the motor.

5. The apparatus of claim 4 wherein the controller includes a microprocessor which is programmable to operate the motor and the pneumatic cylinder according to predetermined schedules of speed and load versus time.

6. The apparatus of claim 5, further comprising a rotatable drive shaft on which the driving element is mounted and a proximity sensor associated with the drive shaft and providing a per-revolution output signal to the controller, the controller being programmed to determine the number of revolutions of the drive shaft from the output signal from the proximity sensor.

7. The apparatus of claim 1 wherein the driving element is a pneumatic chuck having leaves which are outwardly expandable for engaging the inner surface of a sample paper core.

8. The apparatus of claim 7 wherein the leaves of the pneumatic chuck are expandable over a range of outward movement so to be engageable with sample paper cores of varying internal diameter, and wherein the force imparted on the inner surface of the sample paper core by the leaves is selectively variable by varying the gas pressure supplied to the pneumatic chuck.

9. The apparatus of claim 8, further comprising a pressure regulator connected to the pneumatic chuck for varying the gas pressure supplied thereto.

10. The apparatus of claim 1 wherein the driving element comprises a chuck having outwardly expandable leaves which are adapted to collectively contact substantially more than 50 percent of the circumference of the core inner surface.

11. The apparatus of claim 1 wherein the variable-tension belt assembly further includes a pulley mounted on a shaft which is supported by a support plate such that the shaft is freely rotatable about a longitudinal axis thereof, the belt being looped around the pulley, the support plate being movable with respect to the driving element so as to vary the distance between the respective longitudinal axes of the driving element and the shaft, the actuator being connected to the support plate and adapted to move the support plate to effect a change in belt tension.

12. A method of testing dynamic strength of a sample paper core, comprising:
    supporting the sample paper core on a rotatable driving element which engages an inner surface of the sample paper core such that rotation of the driving element causes rotation of the sample paper core about a longitudinal axis thereof;
    applying a load to the sample paper core via an endless flexible belt which is partially looped around an outer surface of the sample paper core and tensioned; and
    rotatably driving the driving element and sample paper core while the load is applied thereto.

13. The method of claim 12 further comprising the step of varying the tension in the belt as a function of time during rotation of the sample paper core.

14. The method of claim 13 further including the step of varying the rotational speed of the driving element as a function of time.

15. The method of claim 12 wherein the step of applying a load to the sample paper core comprises tensioning the belt by actuating a pneumatic cylinder so as to move a rotatable pulley around which the belt is looped away from the rotational axis of the driving element, the pulley being rotatably supported by a support member which is connected to the pneumatic cylinder, and wherein the step of varying the tension in the belt comprises varying gas pressure applied to the pneumatic cylinder so as to vary the force imparted on the support member.

16. The method of claim 15 wherein the step of varying the belt tension comprises varying the gas pressure applied to the pneumatic cylinder via a controllable servo valve and a controller connected to the servo valve, the controller being adapted to operate the servo valve to vary the gas pressure applied to the pneumatic cylinder as a function of time.

17. The method of claim 16 wherein the step of varying the belt tension further comprises measuring the actual force imparted on the support member by the pneumatic cylinder via a load cell which provides an output signal indicative of the actual force, and controlling the force by a microprocessor-based controller which receives the output signal from the load cell and operates the pneumatic cylinder in a feedback loop to drive the actual force toward the desired force.

18. The method of claim 12 wherein the step of supporting the sample paper core comprises supporting the sample paper core on a chuck having outwardly expandable leaves which are adapted to contact substantially more than 50 percent of the circumference of the inner surface of the sample paper core.

19. The method of claim 12 wherein the step of supporting the sample paper core comprises supporting the sample paper core on a pneumatic chuck having outwardly expandable leaves, the leaves being inserted into the sample paper core and gas pressure being applied to the pneumatic chuck to cause the leaves to expand outwardly so as to engage the inner surface of the sample paper core.

20. The method of claim 19 further comprising the step of determining the number of revolutions to failure of the sample paper core by counting the number of revolutions of the pneumatic chuck from start of a test to failure of the paper core.

21. The method of claim 20 wherein the step of rotatably driving the pneumatic chuck comprises rotatably driving a drive shaft on which the pneumatic chuck is mounted, the drive shaft including a proximity sensor providing a per-revolution output signal, and wherein the step of counting the number of revolutions to failure comprises supplying the output signal from the proximity sensor to a microprocessor-based controller which processes the output signal to count the number of revolutions to failure.

22. The method of claim 21 wherein the step of counting the number of revolutions to failure further comprises detecting a failure of the sample paper core and supplying a stop signal to the controller upon detection of the failure, the controller being programmed to stop counting revolutions of the drive shaft upon receipt of the stop signal.

\* \* \* \* \*